United States Patent
Howell

[19]

[11] Patent Number: 5,830,190
[45] Date of Patent: *Nov. 3, 1998

[54] PROTECTED NEEDLE CATHETER PLACEMENT DEVICE HAVING NEEDLE PLACEMENT VISUALIZATION FEATURES AND METHOD FOR ITS USE

[75] Inventor: Glade Harold Howell, Sandy, Utah

[73] Assignee: Becton Dickinson and Company, Franklin Lakes, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 661,685

[22] Filed: Jun. 11, 1996

[51] Int. Cl.$^6$ .................................................. A61M 5/178
[52] U.S. Cl. ........................ 604/168; 604/164; 604/192; 604/198
[58] Field of Search ................................... 604/164, 165, 604/166, 167, 168

[56] References Cited

U.S. PATENT DOCUMENTS

| | | | |
|---|---|---|---|
| Re. 34,416 | 10/1993 | Lemieux | 604/164 |
| 2,737,950 | 3/1956 | Berthiot | 128/218 |
| 3,589,361 | 6/1971 | Loper et al. | 128/214.4 |
| 4,193,399 | 3/1980 | Robinson | 128/214.4 |
| 4,200,096 | 4/1980 | Charvin | 128/214.4 |
| 4,317,445 | 3/1982 | Robinson | 128/214.4 |
| 4,365,630 | 12/1982 | McFarlane | 128/214.4 |
| 4,654,031 | 3/1987 | Lentz | 604/168 |
| 4,676,783 | 6/1987 | Jagger et al. | 604/171 |
| 4,747,831 | 5/1988 | Kulli | 604/110 |
| 4,762,516 | 8/1988 | Luther et al. | 604/164 |
| 4,767,408 | 8/1988 | McFarlane | 604/168 |
| 4,772,265 | 9/1988 | Walter | 604/164 |
| 4,772,267 | 9/1988 | Brown | 604/168 |
| 4,781,692 | 11/1988 | Jagger et al. | 604/164 |
| 4,828,548 | 5/1989 | Walter | 604/164 |
| 4,832,696 | 5/1989 | Luther et al. | 604/164 |
| 4,838,869 | 6/1989 | Allard | 604/195 |
| 4,894,052 | 1/1990 | Crawford | 604/63 |
| 4,900,307 | 2/1990 | Kulli | 604/110 |
| 4,904,242 | 2/1990 | Kulli | 604/110 |
| 4,908,021 | 3/1990 | McFarlane | 604/168 |
| 4,909,793 | 3/1990 | Vining et al. | 604/164 |
| 4,936,830 | 6/1990 | Verlier | 604/110 |
| 4,950,252 | 8/1990 | Luther et al. | 604/198 |
| 4,978,343 | 12/1990 | Dysarz et al. | 604/195 |
| 4,978,344 | 12/1990 | Dombrowski et al. | 604/198 |
| 5,000,740 | 3/1991 | Ducharme et al. | 604/168 X |

(List continued on next page.)

FOREIGN PATENT DOCUMENTS 0 467 703 A1  1/1992  European Pat. Off. .
0 653 220 A1  5/1995  European Pat. Off. .

*Primary Examiner*—Sam Rimell
*Assistant Examiner*—Deborah Blyveis
*Attorney, Agent, or Firm*—Eric M. Lee

[57] ABSTRACT

An over-the-needle catheter placement assembly includes an elongate catheter with an open bore therethrough. The catheter has a tapered distal end and a proximal end with a hub. The assembly includes an elongate hollow handle with a distal end that has an opening therethrough and a proximal end. Included in the assembly is an elongate needle with a sharp distal point, a proximal end and an open passageway therethrough. The assembly has a substantially transparent elongate needle hub with a distal end portion with the proximal end of the needle fixedly attached therein. The needle is coaxially slidably disposed within the catheter bore with the catheter hub mounted on the distal end portion of the needle hub so that the sharp distal pointed end of the needle projects beyond the tapered distal end of the catheter. The needle hub is slidably disposed for coaxial movement within the hollow handle between a first position where the distal end portion of the hub axially projects through the distal opening in said hollow handle so that the needle is distally outside the hollow handle and within the catheter bore and a proximal position to withdraw the needle into the handle. There is an elongate flashback chamber within the needle hub also that is fluidly connected to the proximal end of the needle and extends into the distal end portion of the needle hub.

3 Claims, 6 Drawing Sheets

U.S. PATENT DOCUMENTS

| | | | |
|---|---|---|---|
| 5,032,116 | 7/1991 | Peterson et al. | 604/168 |
| 5,066,284 | 11/1991 | Mersch et al. | 604/168 |
| 5,102,394 | 4/1992 | Lasaitis et al. | 604/164 |
| 5,120,317 | 6/1992 | Luther | 604/168 |
| 5,120,319 | 6/1992 | VanHeugten et al. | 604/168 |
| 5,125,414 | 6/1992 | Dysarz | 128/763 |
| 5,127,905 | 7/1992 | Lemieux | 604/164 |
| 5,129,884 | 7/1992 | Dysarz | 604/164 |
| 5,171,218 | 12/1992 | Fonger et al. | 604/164 |
| 5,242,398 | 9/1993 | Knoll et al. | 604/101 |
| 5,246,426 | 9/1993 | Lewis et al. | 604/168 |
| 5,273,540 | 12/1993 | Luther et al. | 604/110 |
| 5,295,970 | 3/1994 | Clinton et al. | 604/168 |
| 5,487,734 | 1/1996 | Thorne et al. | 604/195 |
| 5,501,675 | 3/1996 | Erskine | 604/164 X |
| 5,573,510 | 11/1996 | Isaacson | 604/164 X |

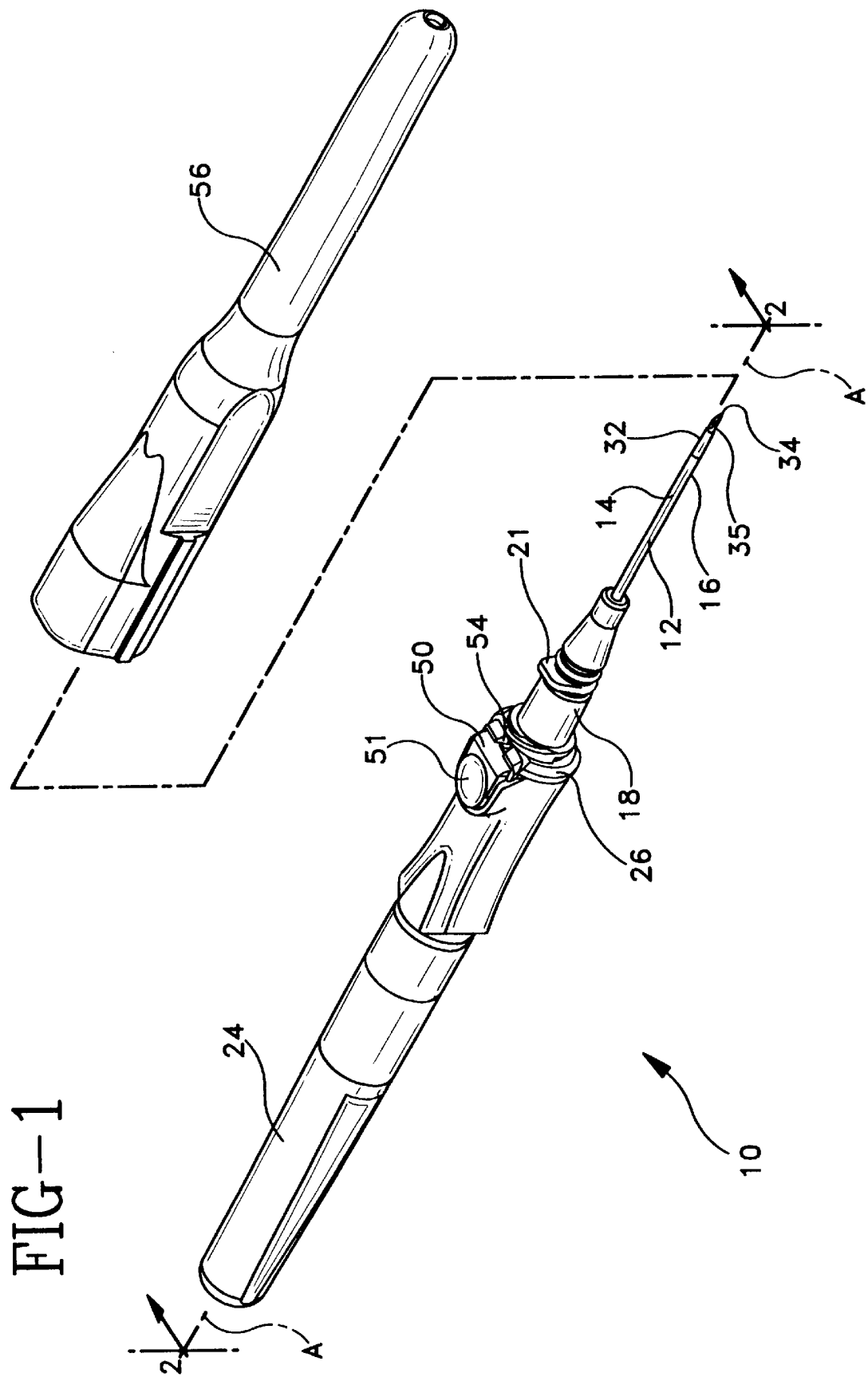

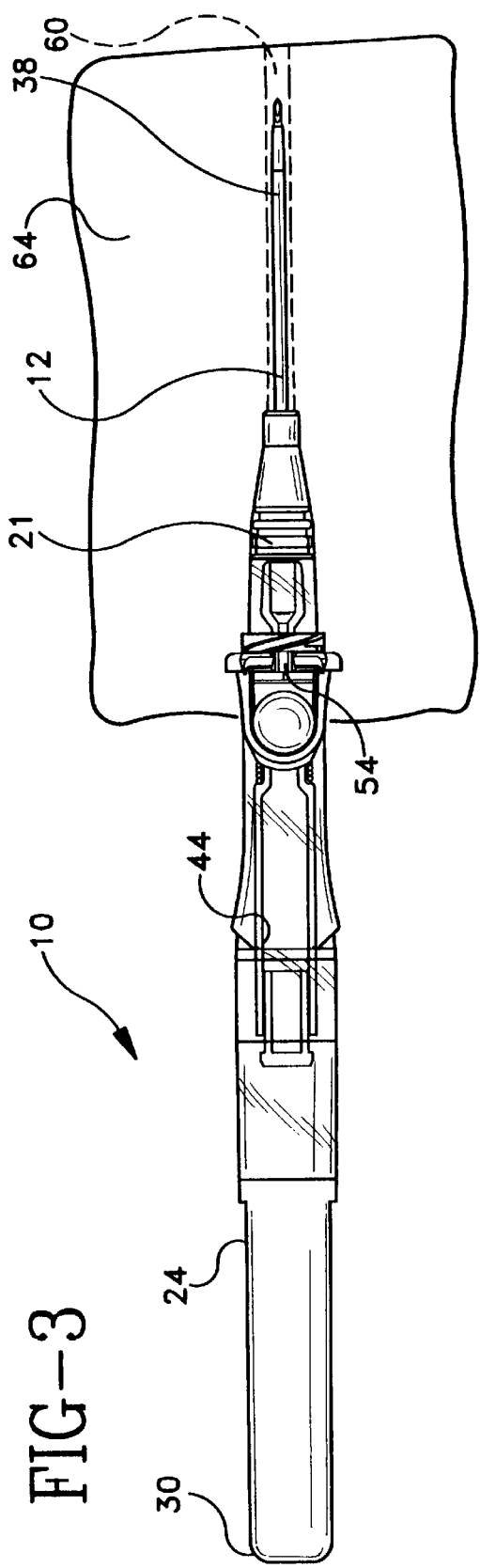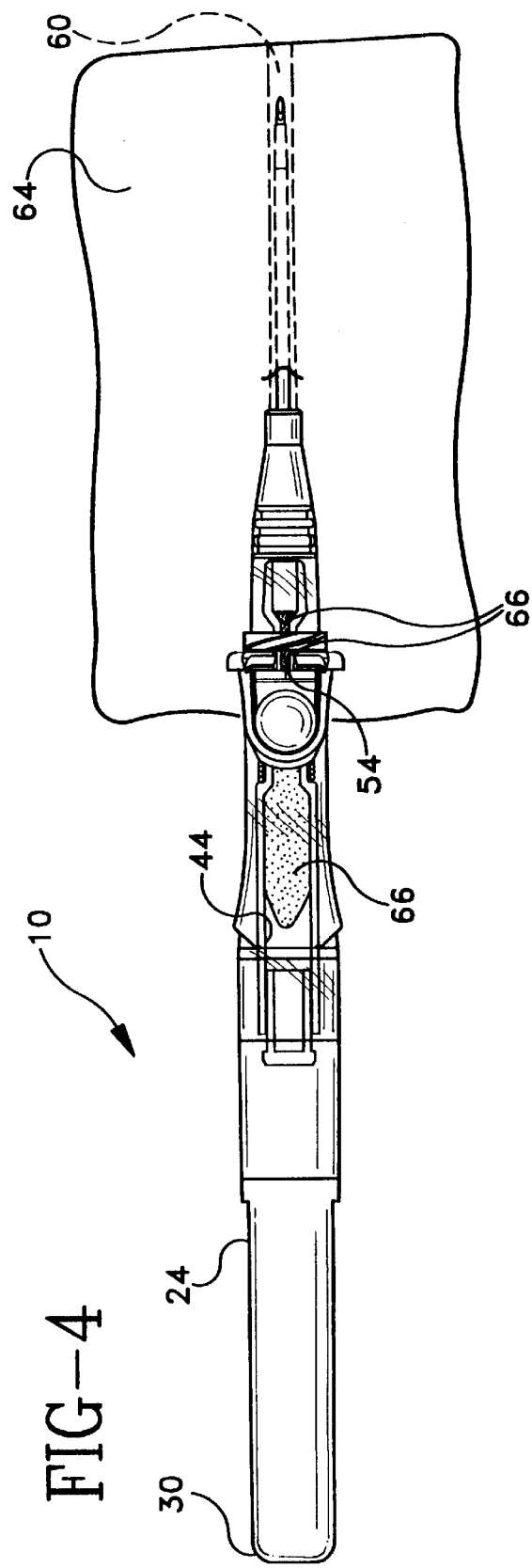

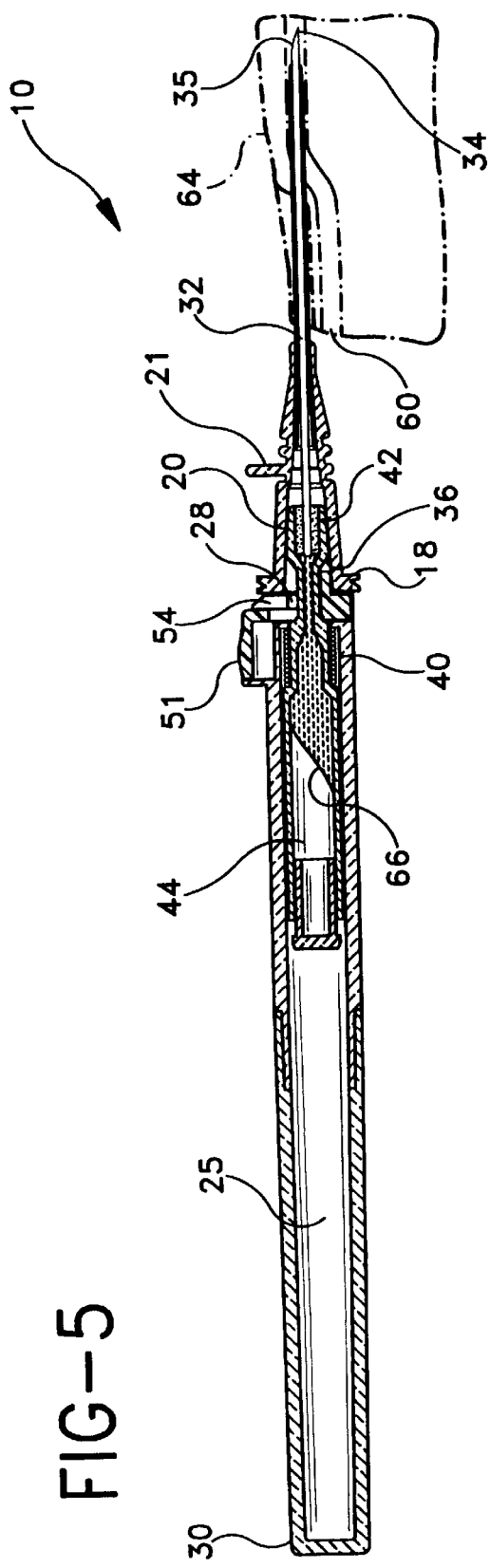
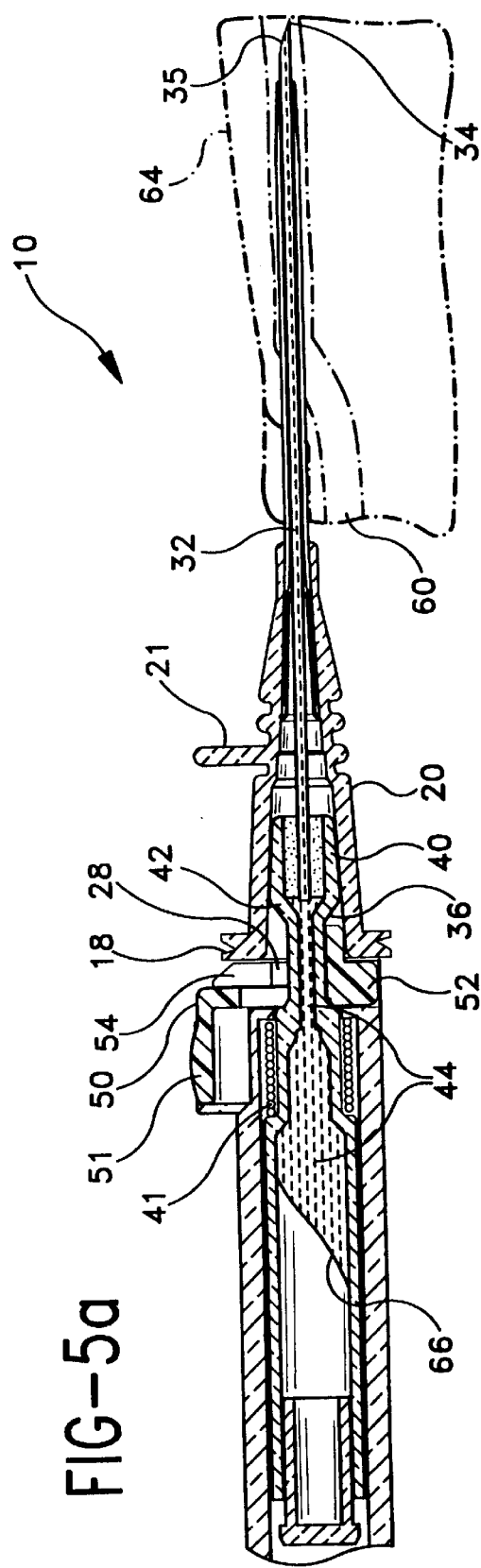

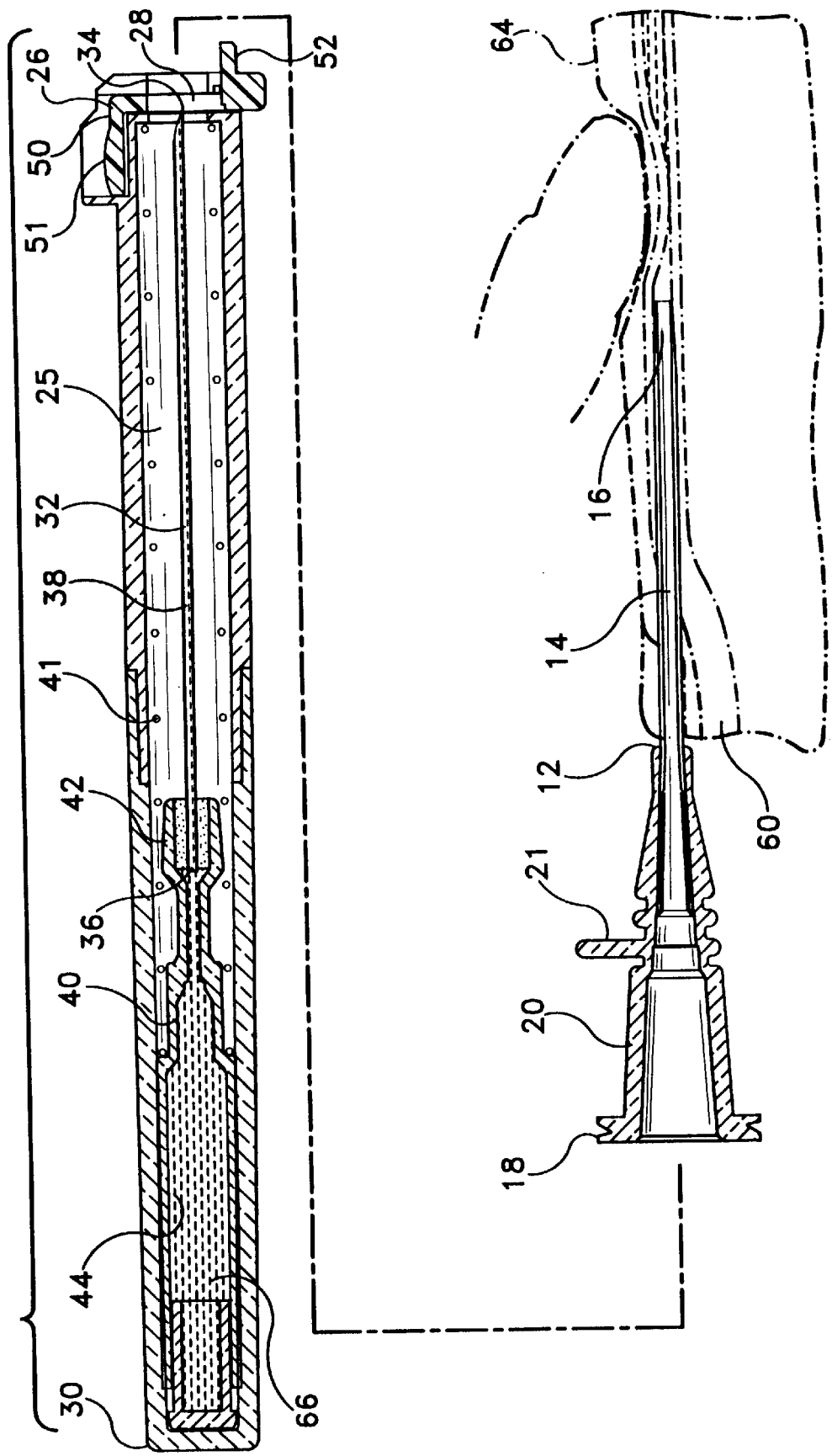

PROTECTED NEEDLE CATHETER PLACEMENT DEVICE HAVING NEEDLE PLACEMENT VISUALIZATION FEATURES AND METHOD FOR ITS USE

FIELD OF INVENTION

This invention is generally related to intravascular catheters and devices for placing an intravascular catheter and more particularly to a catheter placement device with a protected needle retraction system having needle placement visualization features.

BACKGROUND

An intravascular catheter is generally a flexible small diameter tube inserted into a patient's blood vessel to allow withdrawal or addition of fluid. Typically, a practitioner places the intravascular catheter by locating a target blood vessel for the placement, then pierces the patient's skin and the blood vessel wall with an inserter needle, uses the needle to lead the catheter into the vessel and then removes the needle, leaving the catheter in the vessel. Catheters may be inserted into blood vessels either through the bore of the needle or over-the-needle. In this disclosure, catheters that are inserted over-the-needle are described. Additionally, a convention is followed using the term "proximal" to refer to the portion of the device closest to the practitioner and the term "distal" for the portion of the device toward the patient or away from the practitioner.

Over-the-needle catheters are generally supplied already mounted on an inserter needle in a sterile, ready-to-use, unit package. In its simplest form, the over-the-needle catheter generally resembles one tube slidably fit within another tube, the flexible catheter being outermost with a sharp beveled point inserter needle slidably fit within the catheter bore so that the sharp distal inserter needle point projects beyond a gently tapered distal end of the catheter. In placement of these over-the-needle catheters, the needle, with the catheter outside, is held by the practitioner, generally with the point bevel face up, longitudinally aligned with the target blood vessel. The needle is then inserted at a shallow angle through the patient's skin into the blood vessel. The practitioner then often determines that the needle is properly positioned within the blood vessel by allowing a small quantity of the patient's blood to flow through the hollow needle, impelled by the patient's blood pressure, so that the small quantity of blood can be seen at the rear of the needle. This practice of using the patient's blood to signal proper placement of needle within the target vessel is termed "flashing or flashback." The flashing step has the purpose of confirming that the catheter is properly inserted into the blood vessel. Once the proper placement is confirmed, the practitioner applies finger pressure to the vessel over the distal tip of the needle and the catheter to occlude further blood flow, withdraws the needle and attaches a fluid handling device to the catheter hub.

During these manipulative steps, small amounts of the patient's blood may be released. Additionally, once the inserter needle is removed, it is a "blood-contaminated sharp" and must be properly handled. With the recognition by the medical device art of the risk of transmission of Acquired Immunosuppressive Deficiency Syndrome (AIDS) by blood contaminated sharps, devices such as disclosed in U.S. Pat. No. 4,747,831 were developed. The patent discloses a cannula insertion set with a retracting needle. The device disclosed in the patent provides a cannula insertion needle projecting from a hollow handle into which the needle is withdrawn after the placement is completed. Anyone handling the device following the withdrawal is thus substantially protected from the contaminated needle because it is contained within the inserter handle.

A penetration of the far wall of the blood vessel may occur if the practitioner does not stop advancing the needle as soon as it enters the blood vessel. In previous catheter assemblies with needle withdrawal capabilities, the flashback chamber is only located within the hollow handle. Visualization of flashing in these previous devices requires that a significant blood volume be drawn into the chamber before it is visible to the practitioner. Additionally, the practitioner must change the focus of attention from the penetration sight to the hollow handle to observe the flashback. Although the referenced devices have provided significant advances to the medical device art, there is still a need for a retractable needle cannula insertion device that provides the practitioner with yet more rapid confirmation that the needle is properly placed in the patient's blood vessel. Such a device and a method for its use are described below.

SUMMARY

An over-the-needle catheter placement assembly of the present invention includes an elongate catheter with an open bore therethrough. The catheter has a tapered distal end and a proximal end with a hub. The assembly includes an elongate hollow handle with a distal end that has an opening therethrough and a proximal end. The assembly of the invention also has an elongate needle with a sharp distal point, a proximal end and an open passageway therethrough. The assembly has an elongate needle hub with a distal end portion that has the proximal end of the needle fixedly attached therein. The needle hub also includes an elongate flashback chamber within it that is fluidly connected to the proximal end of the needle. The needle hub and needle are slidably disposed for coaxial movement within the hollow handle from a first position to a proximal position within the handle. In the first position, the distal end portion of the hub axially projects through the distal opening in said hollow handle so that the needle is distally outside the hollow handle and within the catheter bore. In the first position, the flashback chamber extends into the distal end portion of the needle hub beyond the distal end of the hollow handle that is within the catheter hub. When the needle hub is in the proximal position, the needle is withdrawn from within the catheter, and the sharp distal needle point is substantially contained within the hollow handle. The hollow handle further includes a latch that releasably retains the needle hub in the first position and a latch release to release the needle hub for the proximal axial movement.

A method for placing a catheter in a blood vessel of a patient using the catheter placement assembly of the present invention includes positioning the assembly so that it is substantially longitudinally aligned with the blood vessel of the patient and a face of the needle bevel is upward. The method includes inserting the sharp point of the needle through the patient's skin at an angle less than about thirty degrees so that the needle distal point enters the blood vessel and observing a blood flashback in the flashback chamber in the distal end portion of the needle hub. In the method, observation of the blood flashback at a distal portion of the assembly confirms the placement of the needle in the blood vessel. The method further includes introducing the catheter into the patient's blood vessel by sliding the catheter distally along and off the needle.

The catheter placement assembly of the invention, by having the flashback chamber extend beyond and visible distally to the hollow handle of the assembly, allows the practitioner to recognize almost instantaneously when the needle point has penetrated the vessel wall and entered the patient's blood vessel. The rapid visualization substantially reduces the potential for incidents of needle penetration through the far wall of the blood vessel. In previous catheter assemblies with needle withdrawal capabilities, the flashback chamber is only located within the hollow handle. Visualization of flashing in these previous devices requires that a larger blood volume be drawn into the chamber than the present invention before it is visible to the practitioner. Additionally, in these previous devices the flashback chamber may be partially obscured by the practitioner's hand, the bias element or the release mechanism. In the present invention, the flash chamber is visible distally to the hollow handle, the bias element, the release mechanism and the practitioner's hand.

BRIEF DESCRIPTION OF THE DRAWINGS

FIG. 1 is a partially exploded perspective view of the catheter placement device of the present invention;

FIG. 3 is a top plan view of the invention of FIG. 1 with the shield removed, and the catheter and needle aligned for placement into a patient;

FIG. 4 is a top plan view of the invention of FIG. 1 illustrating placement of the device into a patient's blood vessel;

FIG. 5 is a cross-sectional view, analogous to FIG. 2, of the invention of FIG. 1 as placed in a patient's blood vessel;

FIG. 5a is an enlarged view, analogous to FIG. 2a, of the view of FIG. 5; and

FIG. 6 is a cross-sectional view of the invention of FIG. 1, after release of the needle withdrawal mechanism with the catheter ready for use.

DETAILED DESCRIPTION

Figure 1A:
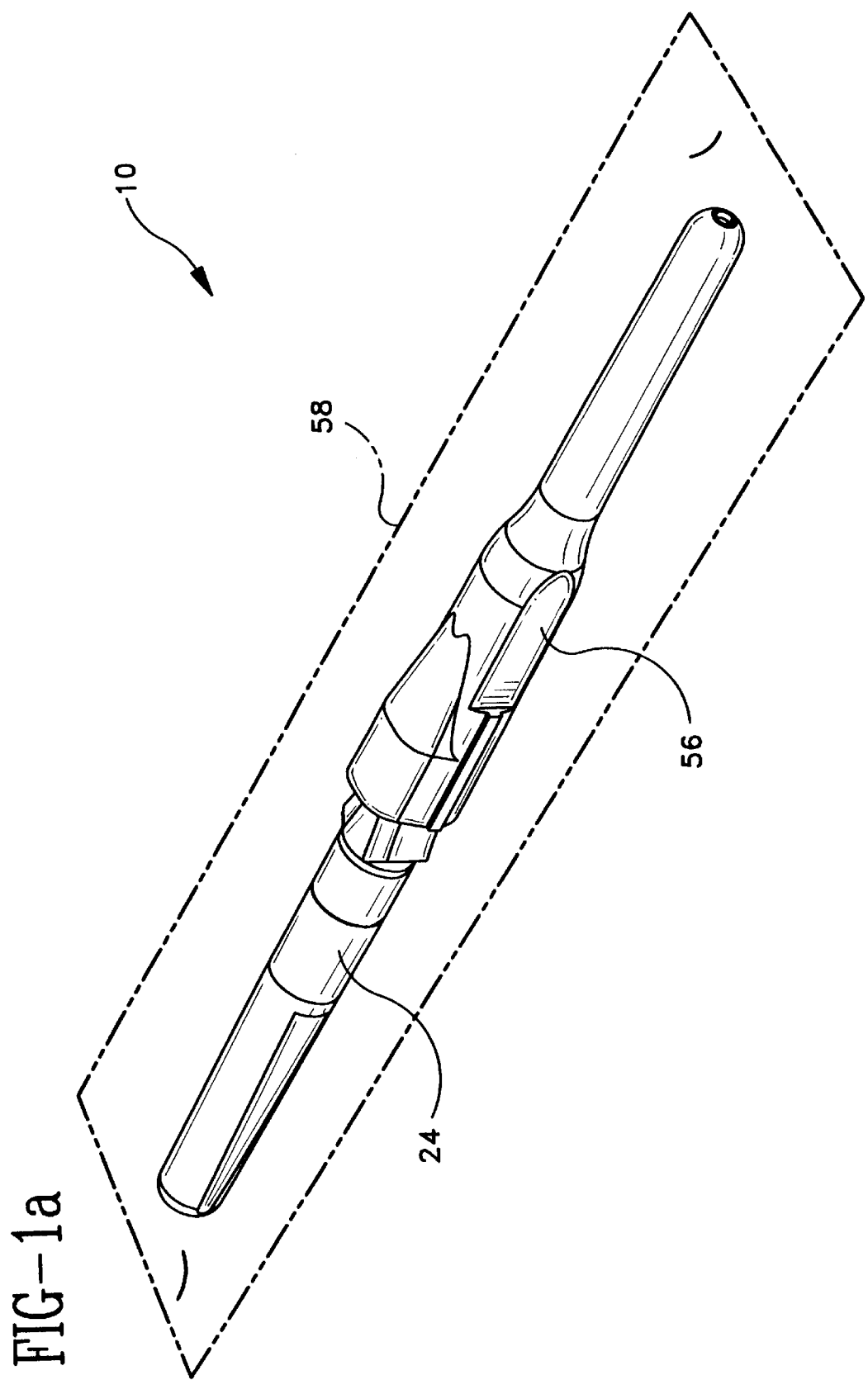
FIG. 1a illustrates the invention of FIG. 1 assembled and placed in a package.
Figure 2:
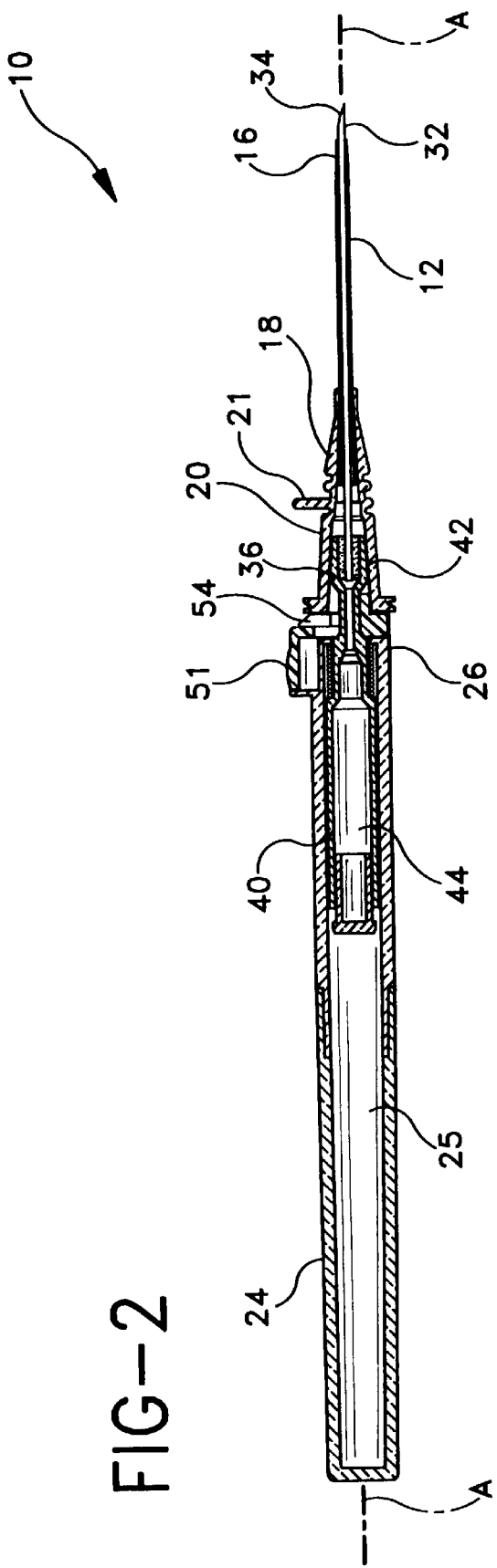
FIG. 2 is a cross-sectional view of the invention of FIG. 1 taken along the line 2—2.
Figure 2A:
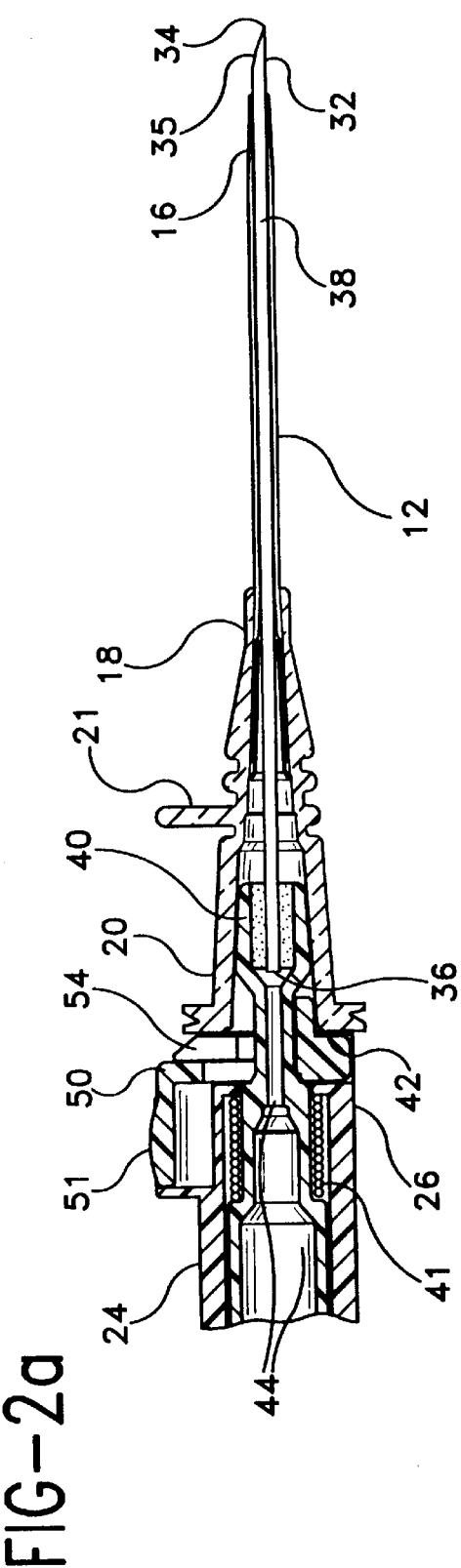
FIG. 2a is an enlarged view of a portion of the view of FIG. 2.

While this invention is satisfied by embodiments in many different forms, there is shown in the drawings and is herein described in detail, a preferred embodiment of the invention with the understanding that the present disclosure is to be considered exemplary of the principles of the invention and is not considered to limit the invention to the embodiment illustrated. The scope of the invention is measured by the appended claims and their equivalents.

Referring to FIGS. 1–6, a preferred needle assembly 10 of the present invention with a longitudinal axis A includes an elongate catheter 12 with an open bore 14 therethrough, a tapered distal end 16 and a proximal end 18 with a hub 20. Assembly 10 has an elongate hollow handle,24 that has a cavity 25 therewithin. Hollow handle 24 has a distal end 26 that has an opening 28 therethrough into cavity 25 and a proximal end 30. Assembly 10 also has an elongate needle 32 that has a sharp distal point 34, preferably having a beveled surface 35, a proximal end 36 and an open passageway 38 therethrough. Preferred assembly 10 has a substantially transparent, or at least translucent, elongate needle hub 40 with a distal end portion 42 with needle proximal end 36 fixedly attached therein. Needle hub 40 also has an elongate flashback chamber 44 that is fluidly connected to open passageway 38 at proximal end 36 of the needle. Flashback chamber 44 extends into distal end portion 42 of the needle hub. Needle hub 40 and needle 32 are slidably disposed for coaxial movement within the cavity in hollow handle 24 from a first position, best seen in FIGS. 5 and 5a, to a proximal position. In the first position distal end portion 42 of the needle hub projects axially outwardly from the hollow handle through opening 28. When needle hub 40 is in the first position, needle 32 is outside of and axially distal to the hollow handle. Needle 32 is also coaxially slidably disposed within catheter bore 14 so that sharp distal pointed end 34 of the needle projects beyond the tapered distal end of the catheter and catheter hub 20 is releasably mounted onto distal end portion 42 of the needle hub. Prior to use, when needle hub 40 is in the first position with catheter 12 mounted on the distal end portion, flashback chamber 44 preferably extends into catheter hub 20. Catheter hub 20 is formed from a substantially transparent, or at the least translucent, material, so that flashback chamber 44 in the distal end portion of the needle hub is visible through the catheter hub.

Needle hub 40 is operatively biased, preferably by a coil spring 41, for coaxial movement from the first position to a proximal position, best seen in FIG. 6, where the needle with the sharp distal point is withdrawn into cavity 25 to be substantially within the hollow handle. Hollow handle 24 includes a releasable latch 50, with a trigger 51 for releasing the latch, that engages needle hub 40 to retain the needle hub in the first position and, disengages, when actuated by the practitioner, to release the needle hub for movement to the proximal position within the hollow handle. Trigger 51 is preferably located at, or a proximal distance from, distal end 26 of the hollow handle.

The assembly of the present invention further includes provisions to allow the practitioner to see the flashback chamber in the distal end portion of the hub. Preferably, distal end 26 of the hollow handle has a slot 54, located distally to latch 50 that provides direct visual access to the flashback chamber in distal end portion 42 of the hub. As discussed above, the hub is formed from a material that is substantially transparent, or at the least translucent. Thus, since the distal end portion of the needle hub projects beyond the hollow handle, blood flashback from the patient present in the flashback chamber at proximal end 36 of the needle, is immediately visible to the practitioner. Unlike the referenced earlier needle assemblies, the practitioner's view of the blood flashback is not obstructed by the bias spring, the latch or the practitioner's hand. Additionally, since the hollow handle also is preferably formed from a substantially transparent, or at least translucent, material, the practitioner is able to see the rest of the flashback chamber that is within the rest of the needle hub that is within the hollow handle.

Referring to FIGS. 1 and 1a, assembly 10 is preferably supplied with a shield 56, sized and shaped to fit onto hollow handle 24 to obstruct inadvertent access to needle 32 and trigger 51 for releasing latch 50. Preferably, assembly 10 with shield 56 is placed within a sealed package 58, as indicated in phantom in FIG. 1a, that is formed from materials substantially resistant to the passage of microorganisms. The sealed package is then preferably exposed to conditions sufficient to render any microorganisms within the package substantially non-viable. Suitable package materials include, but are not limited to, paper, plastic film, non-woven materials, combinations thereof and the like. Suitable conditions for rendering microorganisms non-viable include, but are not limited to, chemical sterilants such as ethylene oxide, hydrogen peroxide vapor and the like; and exposure to ionizing radiation such as gamma radiation, beta particles and the like. The packaged assembly is then considered to be sterile until the package is opened. When materials are selected for forming assembly 10 and package 58, there should be consideration of the particular materials' compatibility with the planned sterilization conditions.

Suitable materials for forming hollow handle 24, catheter hub 20 and needle hub 40 include, but are not limited to, thermoplastic polymeric resins such as polycarbonate, polystyrene, polypropylene and the like. Needle 32 and coil spring 41 are preferably formed from a stainless steel alloy and the like.

Preferably, when assembly 10 is manufactured, needle 32 is rotationally oriented in hub 40 so beveled surface 35 is substantially aligned with trigger 51 for releasing latch 50. Further, catheter hub 20 preferably includes an outwardly projecting tab 21 that is also substantially aligned with the beveled surface and the trigger when the catheter hub is mounted on the needle hub. The alignment of the needle point beveled surface, the catheter hub tab and the trigger provides for an intuitive and ergonomic usage of the assembly. When the assembly is unshielded in preparation for usage by the practitioner, the alignment of the needle bevel and trigger substantially directs the practitioner's grasp of the hollow handle to the proper position for insertion into the patient with needle point bevel surface 35 facing upward as shown in FIG. 3.

Referring to FIGS. 5, 5a and 6, latch 50 preferably includes a projection 52 that is contained within catheter hub 20 when the catheter is fully mounted on needle hub 40 as shown in FIGS. 5 and 5a. Projection 52 substantially prevents inadvertent actuation of latch 50 while catheter hub 20 is mounted on needle hub 40 by preventing movement of the latch. When catheter hub 20 is dismounted from needle hub 40 as the catheter is advanced into the patient's blood vessel, projection 52 is no longer contained within catheter hub 20 and the practitioner's actuation of trigger 51 is able to urge latch 50 from the position where it retains needle hub 40 in the distal position to a position where the needle hub is no longer retained. The bias provided by spring 41 then urges the needle hub to the proximal position.

A preferred method for a practitioner to place a catheter into a patient's target blood vessel 60 using assembly 10 of the present invention is illustrated in FIGS. 3–6. The method includes opening package 58, removing the shielded assembly 10 then dismounting shield 56 and exposing catheter 12 with projecting needle point 34. The method includes positioning assembly 10 substantially longitudinally aligned with target blood vessel 60 with bevel 35 facing substantially away from a surface 64 of the skin, as shown in FIG. 3, and inserting it at a shallow angle, preferably less than about 35 degrees, into surface 64 of the skin, so that distal point 34 enters target blood vessel 60, as shown in FIGS. 4, 5 and 5a. The method then includes observing a blood flashback 66 in blood flashback chamber 44 in distal end portion 42 of the needle hub through slot 54, or through the preferably transparent catheter hub, as best seen in FIGS. 4, 5 and 5a. After confirming placement of needle 32 in the target blood vessel, the method includes advancing catheter 12 distally axially along needle 32 into position in the blood vessel, preferably using upwardly extending tab 21. As placement of the catheter is achieved, the method includes the practitioner placing a finger from his other hand on the patient's skin over the blood vessel. By placing his finger on the patient's skin and applying sufficient pressure on the skin, the practitioner thereby occludes blood flow through the catheter, as shown in FIG. 6. The method then includes the practitioner withdrawing the needle from bore 14 of the catheter by depressing trigger 51 and releasing latch 50 so that the bias spring urges needle hub 42 into the proximal position within hollow handle 24. The practitioner may then attach any desired fluid handling device to the catheter hub and commence the planned treatment. The handle with the needle substantially within it may then be disposed of according to the facility's disposal protocol.

The needle hub of the invention with the flashback chamber distally extended into and visible through the catheter hub may be beneficially incorporated into catheter/needle placement assemblies where the placement needle is not retractable and such applications are considered within the scope of the invention. In any over-the-needle catheter placement, the practitioner's attention is necessarily focused on the penetration site. The needle hub of the invention allows the practitioner to observe flashback without having to divert attention away from the penetration site.

The catheter placement assembly of the invention, by having the flashback chamber extend beyond and being visible distally to the hollow handle of the assembly, allows the practitioner to recognize almost instantaneously when the needle point has penetrated the vessel wall and entered the patient's blood vessel. This rapid visualization of flashback substantially reduces the potential for incidents of needle penetration through the far wall of the blood vessel by allowing the practitioner to stop advancing the needle as soon as it enters the blood vessel.

What is claimed is:

1. An introducer needle and catheter assembly comprising:

an elongate hollow handle having a distal end with an axial opening therethrough and a proximal end, the distal end of the elongate hollow handle defining a radial opening therein;

an elongate needle having a sharp distal end, a proximal end and an open passageway therethrough;

a translucent needle hub having a distal end connected to the proximal end of the elongate needle, wherein a portion of the translucent needle hub is located adjacent to the distal end of the elongate hollow handle prior to use so a portion of the translucent needle hub is visible through the radial opening at the distal end of the elongate hollow handle;

a catheter having a proximal end and a distal end; and a catheter hub connected to the proximal end of the catheter, wherein the catheter hub is adjacent to the distal end of the elongate hollow handle prior to use but does not cover the radial opening at the distal end of the elongate hollow handle.

2. The introducer needle and catheter assembly of claim 1 further comprising a spring engaging the translucent needle hub to bias the translucent needle hub toward the proximal end of the elongate hollow handle.

3. The introducer needle and catheter assembly of claim 2 further comprising a movable latch that engages the translucent needle hub to hold the translucent needle hub adjacent to the distal end of the elongate hollow handle against the bias of the spring.

* * * * *